US011234779B2

(12) United States Patent
Fuerst et al.

(10) Patent No.: US 11,234,779 B2
(45) Date of Patent: Feb. 1, 2022

(54) HANDHELD USER INTERFACE DEVICE FOR A SURGICAL ROBOT

(71) Applicant: Verb Surgical Inc., Mountain View, CA (US)

(72) Inventors: Bernhard Adolf Fuerst, Sunnyvale, CA (US); Pablo E. Garcia Kilroy, Menlo Park, CA (US)

(73) Assignee: VERB SURGICAL. INC., Santa Clara, CA (US)

( * ) Notice: Subject to any disclaimer, the term of this patent is extended or adjusted under 35 U.S.C. 154(b) by 310 days.

(21) Appl. No.: 16/566,336

(22) Filed: Sep. 10, 2019

(65) Prior Publication Data

US 2021/0068907 A1 Mar. 11, 2021

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/25* (2016.02); *A61B 90/361* (2016.02); *A61B 90/50* (2016.02);
(Continued)

(58) Field of Classification Search
CPC ......... A61B 34/35; A61B 34/25; A61B 90/50; A61B 90/361; A61B 2034/305; A61B 2017/00477; A61B 17/00234; A61B 34/74; A61B 2034/2065; A61B 2034/252; A61B 34/32; A61B 2034/2048; A61B 2090/371; A61B 2090/372; A61B 2090/365; A61B 2034/107
See application file for complete search history.

(56) References Cited

U.S. PATENT DOCUMENTS

2016/0270867 A1 9/2016 Scholan
2017/0195623 A1 7/2017 Stuart et al.
(Continued)

FOREIGN PATENT DOCUMENTS

WO 2018050307 A1 3/2018

OTHER PUBLICATIONS

International Search Report and Written Opinion of the Searching Authority dated Jun. 5, 2020 for PCT/2019/051260.

*Primary Examiner* — Richard G Louis
(74) *Attorney, Agent, or Firm* — Womble Bond Dickinson (US) LLP

(57) ABSTRACT

Disclosed herein is a mobile interface device to control a robotically-assisted surgical system. The mobile interface device provides a surgeon with a direct view of the surgical robotic system and allows a surgeon to easily and intuitively select, control, or manipulate various target components of the surgical robotic system. The mobile interface device may capture a live image of the surgical robotic system to automatically identify a robotic arm that appears in the center of the captured live image as the target component selected by the surgeon. Based on the current pose or position of the target component, the mobile interface device may generate a list of target poses and control options. The surgeon may select a control option to select a target pose and to manipulate the target component to command a robotically-assisted movement of the selected robotic arm from the current pose to the target pose.

20 Claims, 7 Drawing Sheets

(51) Int. Cl.
*A61B 90/50* (2016.01)
*A61B 90/00* (2016.01)
A61B 34/30 (2016.01)
A61B 17/00 (2006.01)

(52) U.S. Cl.
CPC .................. *A61B 17/00234* (2013.01); *A61B 2017/00477* (2013.01); *A61B 2034/305* (2016.02)

(56) References Cited

U.S. PATENT DOCUMENTS

2017/0305015 A1 10/2017 Krasny et al.
2019/0183591 A1* 6/2019 Johnson ................... B25J 9/161

* cited by examiner

HANDHELD USER INTERFACE DEVICE FOR A SURGICAL ROBOT

TECHNICAL FIELD

The subject technology generally relates to robotics and surgical systems, and more specifically to a screen-based interface to identify and manipulate components such as surgical robotic arms or other components such as the table of a surgical robotic system for preparing or performing minimally invasive surgeries.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. In robotic MIS systems, it may be desirable to establish and maintain high positional accuracy for surgical instruments supported by the robotic arms.

Existing robotically-assisted surgical systems usually consist of a surgeon console from which a surgeon may select and manipulate the robotic arms and devices attached to the robotic arms. A robot controller may request the surgeon to select a robotic arm by presenting on the surgeon console identifiers such as numbers or mounting positions associated with the multiple robotic arms. Due to the lack of a natural spatial relationship between the robotic arms as viewed by the surgeon at the surgeon console and the robotic arms when seen in a direct view, the surgeon may select the wrong robotic arm. Moving the wrong robotic arm may cause severe harm to the patient, other equipment, or bedside personnel. It is desirable to have an interface that allows a surgeon to control the surgical robotic system in a more intuitive manner to minimize mistakes when performing robotically-assisted surgeries.

SUMMARY

Disclosed herein is a mobile interface device to control a robotically-assisted surgical system, also referred to as a surgical robotic system, which is a software-controlled, electro-mechanical system, designed for surgeons to perform minimally-invasive surgeries. The mobile interface device provides a surgeon with a direct and real-time view of the surgical robotic system and allows a surgeon to easily and intuitively select, control, or manipulate various target components of the surgical robotic system. For example, the mobile interface device may automatically identify a robotic arm that is in the center of attention of the surgeon, or that appears in the center of an image captured by the interface device, as the target component selected by the surgeon. Based on the current pose or position of the target component, the mobile interface device may generate a list of control options. The surgeon may select a control option to manipulate the target component such as commanding a robotically-assisted movement of the selected robotic arm to a desired pose.

The interface device for the surgical robotic system may include a camera, a processor, a display, and one or more control buttons. The camera may capture live images or videos of the surgical robotic system. The processor may execute image processing software on the captured live videos or images to identify a target component of the surgical robotic system to be controlled using the interface device and to determine an initial or a current pose of the target component. The display may display the captured live images or videos including identifying the target component of the surgical robotic system. The display may display one or more potential target poses of the target component. The interface device may present control options to allow the surgeon to select one of the potential target poses and to control the target component. The control buttons may be used to generate input commands to the surgical robotic system to move the target component from the current pose to the selected target pose.

In one aspect, the processor may identify the potential target poses of the target component by processing the captured video or images to identify one or more objects with which the target component may engage. In one aspect, the interface device may receive information on the target pose from the surgical robotic system or through commands entered by the surgeon into the interface device. In one aspect, the interface device may include one or more sensors. The sensors may measure in three-dimensions the relative positions to the interface device of various surface points of the surgical robotic system captured by the camera. The interface device may process the measurements from the sensors to aid in identifying the target component, in determining the current pose of the target component, or in identifying the potential target poses of the target component.

BRIEF DESCRIPTION OF THE DRAWINGS

The accompanying drawings are provided together with the following description of various aspects and embodiments of the subject technology for a better comprehension of the invention. The drawings and the embodiments are illustrative of the invention, and are not intended to limit the scope of the invention. It is understood that a person of ordinary skill in the art may modify the drawings to generate drawings of other embodiments that would still fall within the scope of the invention.

DETAILED DESCRIPTION

Examples of various aspects and variations of the subject technology are described herein and illustrated in the accompanying drawings. The following description is not intended to limit the invention to these embodiments, but rather to enable a person skilled in the art to make and use this invention.

An interface device is disclosed herein to allow surgeons to intuitively control a surgical robotic system, which is a software-controlled, electro-mechanical system designed to help the surgeons perform minimally-invasive surgeries. The interface device allows a surgeon who has a direct view of an operating room environment to select, control, or manipulates various components of the surgical robotic system or accessories attached thereto during the preoperative setup, during the surgery, or during the post-operative procedures. For example, the surgeon may use a portable interface device to select a robotic arm of the surgical robotic system by placing the robotic arm near the center of the field of view of a camera of the interface device. The interface device may automatically identify the robotic arm of interest and may determine its initial or current pose by running image processing on the image of the surgical robotic system captured by the camera. By selecting and controlling components of the surgical robotic system through the direct view provided by the interface device rather than through the indirect view of a remote console, the risk of a surgeon mistakenly selecting and moving the wrong component of the surgical robotic system may be reduced.

Based on the initial pose of the selected component, the interface device may present control options for the selected component. The surgeon may select a control option to activate robotically-assisted movement of the selected component to a target position through a planned trajectory. For example, the surgeon may move a robotic arm from a preparation position to a pre-docking position to engage with an endoscopic instrument or accessories intended for endoscopic manipulation of tissues including grasping, cutting, blunt and sharp dissection, approximation, ligation, electrocautery, and suturing. In another example, the surgeon may change an angle of the surgery table to elevate the feet of a patient to provide the endoscopic instrument with a clearer view of the target issue or organ.

Figure 1:
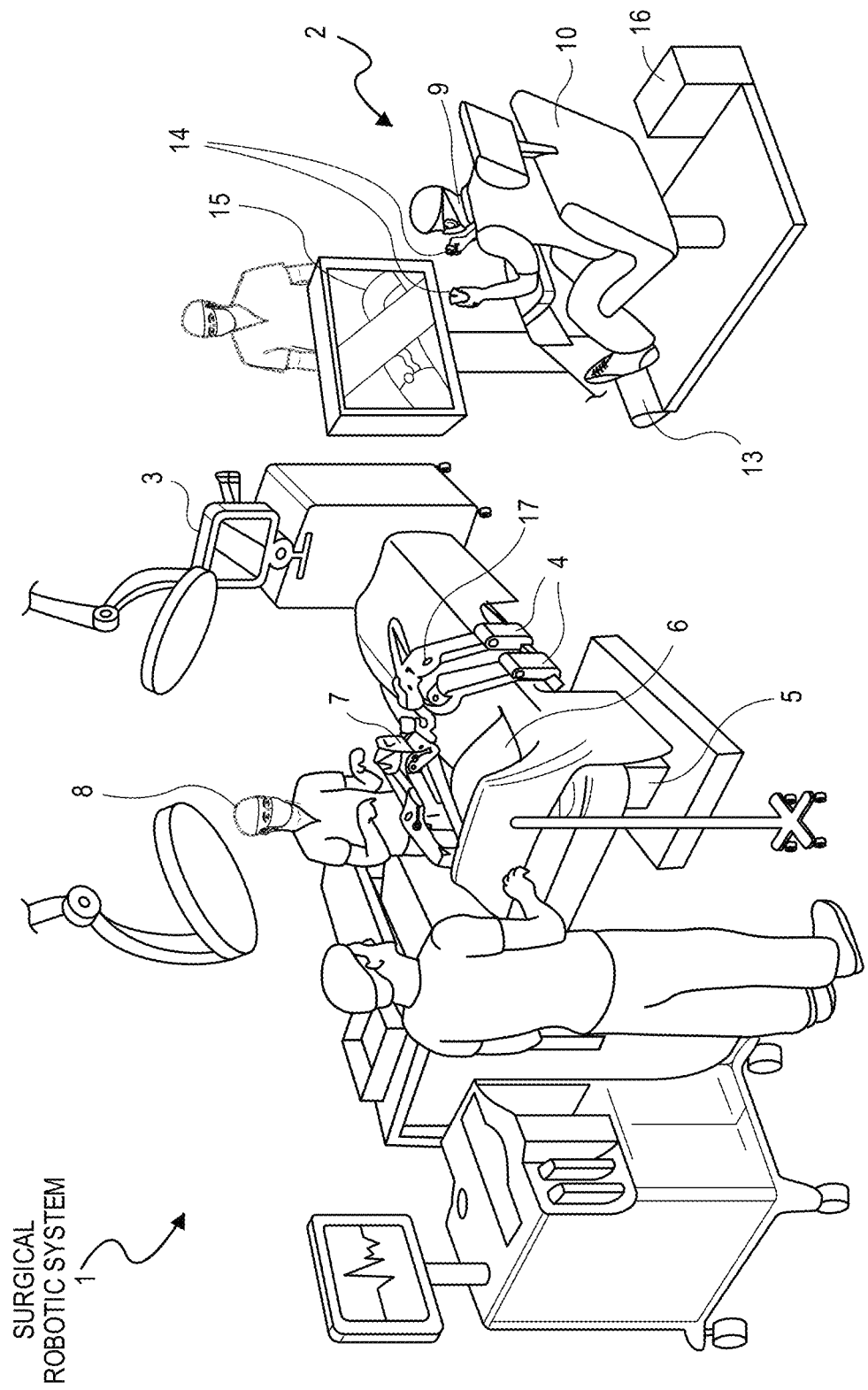
FIG. 1 is a pictorial view of an example surgical robotic system 1 in an operating arena, in accordance with aspects of the subject technology.

FIG. 1 is a pictorial view of an example surgical robotic system 1 in an operating arena, in accordance with aspects of the subject technology. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or another person, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. For example, the remote operator 9 at the user console 2 or the bedside operator 8 may use the handheld UIDs 14 to move the arm 4 from the stowed configuration to a preparation position above the patient 6 during the pre-operative setup. Alternatively, a surgeon or bedside personnel with a direct view of the table 5 may operate the interface device disclosed herein to select and to move an arm 4 to the preparation position. Next, the surgery proceeds with the remote operator 9 at the user console 2 utilising the foot-operated controls 13 and the UIDs 14 to manipulate the various end effectors and perhaps an imaging system, to perform the surgery. Manual assistance may also be provided at the procedure bed or table 5, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilisation and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table 5 to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In one aspect, instead of an arm 4 or the attached surgical tool 7 mimicking the movement of the UID 14 in the hands of the remote operator 9, a surgeon with a direct view of the arm 4 or the surgical tool 7 may use the interface device disclosed herein to move the arm 4 or the surgical tool 7 to a desired position. For example, a surgeon may select one of the arms 4 by framing a target arm near the center of the field of view of a camera of the interface device. The interface device may run image processing software on the image captured by the camera to automatically identify the target arm as the object to be controlled and to determine its initial or current pose. For example, the interface device may identify the arm near the center of the image frame as the target arm and may determine that the target arm is in the preparation position. The interface device may highlight the target arm by displaying a visual indicator on the screen such as by outlining the target arm on the display screen with a green engagement indicator or by rendering an image of the target arm augmented with virtual information. In another aspect, the surgeon may use the touch screen to indicate the object to be controlled by touching the object, for example, by touching the arm 4 displayed on the touch screen.

In one aspect, the interface device may run the image processing software to identify one or more objects or points near the objects in the image frame as a possible destination position for the target arm. The interface device may identify or highlight the possible destination positions on the display screen, may display the names of the possible destination positions on the display screen, and may request the surgeon to confirm the destination position. For example, the interface device may identify a trocar near the target arm as a surgical tool that the target arm may wish to engage, and thus a possible destination position for the target arm, by highlighting the trocar on the screen and requesting the surgeon to confirm. If the surgeon confirms, the interface device may calculate a trajectory for moving the target arm from the preparation position to a pre-docking position proximate to the trocar so the trocar may be attached to the distal end of the target arm. The interface device may display the calculated trajectory as one of the options for the surgeon to select. In another aspect, the surgeon may use the touch screen to indicate the destination position for the target arm by, for example, pressing the trocar displayed on the touch screen. In another aspect, the interface device may display a number of options indicating predefined positions or poses as possible destination positions of the target arm and planned trajectories to the predefined positions for the surgeon to select. Once the surgeon selects the trajectory, position, or pose, the interface device transmits information to the surgical robotic system 1 to enable the surgical robotic system 1 to activate the actuator 17 to drive the gears, linkages, or joints of the target arm to move the target arm through the selected or programmed trajectory to the destination position or pose.

In some aspects, the communication between the platform 5 and the user console 2 or the interface device may be through a control tower 3, which may translate user commands that are received from the user console 2 (and more particularly from the console computer system 16) or from the interface device into robotic control commands that are transmitted to the arms 4 on the robotic platform 5. The control tower 3 may also transmit status and feedback from the platform 5 back to the user console 2 or the interface device. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Prior to initiating surgery with the surgical robotic system 1, the surgical team can perform the preoperative setup. During the preoperative setup, the main components of the surgical robotic system (table 5 and robotic arms 4, control tower 3, and user console 2) are positioned in the operating room, connected, and powered on. The table 5 and robotic arms 4 may be in a fully-stowed configuration with the arms 4 under the table 5 for storage and/or transportation purposes. The surgical team can extend the arms from their stowed position for sterile draping. After draping, the arms 4 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 4 over the patient and attach each arm to its corresponding sleeve. The surgical robotic system 1 has the capability to uniquely identify each tool (endoscope and surgical instruments) as soon as it is attached and display the tool type and arm location on the open or immersive display 15 at the user console 2 and the touchscreen display on the control tower 3. The corresponding tool functions are enabled and can be activated using the master UIDs 14 and foot pedals 13. The patient-side assistant can attach and detach the tools, as required, throughout the procedure. The surgeon seated at the user console 2 can begin to perform surgery using the tools controlled by two master UIDs 14 and foot pedals 13. The system translates the surgeon's hand, wrist, and finger movements through the master UIDs 14 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 14 for instrument alignment and continue instrument control and motion. The foot pedals 13 may be used to activate various system modes, such as endoscope control and various instrument functions including monopolar and bipolar cautery, without involving surgeon's hands removed from the master UIDs 116.

The table 5 can be repositioned intraoperatively. For safety reason, all tool tips should be in view and under active control by the surgeon at the user console 2. Instruments that are not under active surgeon control must be removed, and the table feet must be locked. During table motion, the integrated robotic arms 4 may passively follow the table movements. Audio and visual cues can be used to guide the surgery team during table motion. Audio cues may include tones and voice prompts. Visual messaging on the displays at the user console 2 and control tower 3 can inform the surgical team of the table motion status.

In one aspect, a surgeon with a direct view of the table 5 may use the interface device disclosed herein to reposition the table 5. For example, a surgeon may wish to elevate the upper torso of the patient 6. The surgeon may select a section of the table 5 that holds the patient's upper torso by framing the table section near the center of the field of view of the camera. The interface device may run image processing software on the camera image to identify the table section as the object to be controlled. In another aspect, the surgeon may use the touch screen to indicate the table section to be controlled by touching the table section. The interface device may present a number of options indicating different degrees by which the table section may be raised or lowered. In one aspect, the surgeon may specify the angle of elevation. Once the surgeon selects or enters the new position of the table section, the interface device transmits information to the surgical robotic system 1 to enable the surgical robotic system 1 to drive the mechanisms to elevate the table section to the desired position.

Figure 2A:
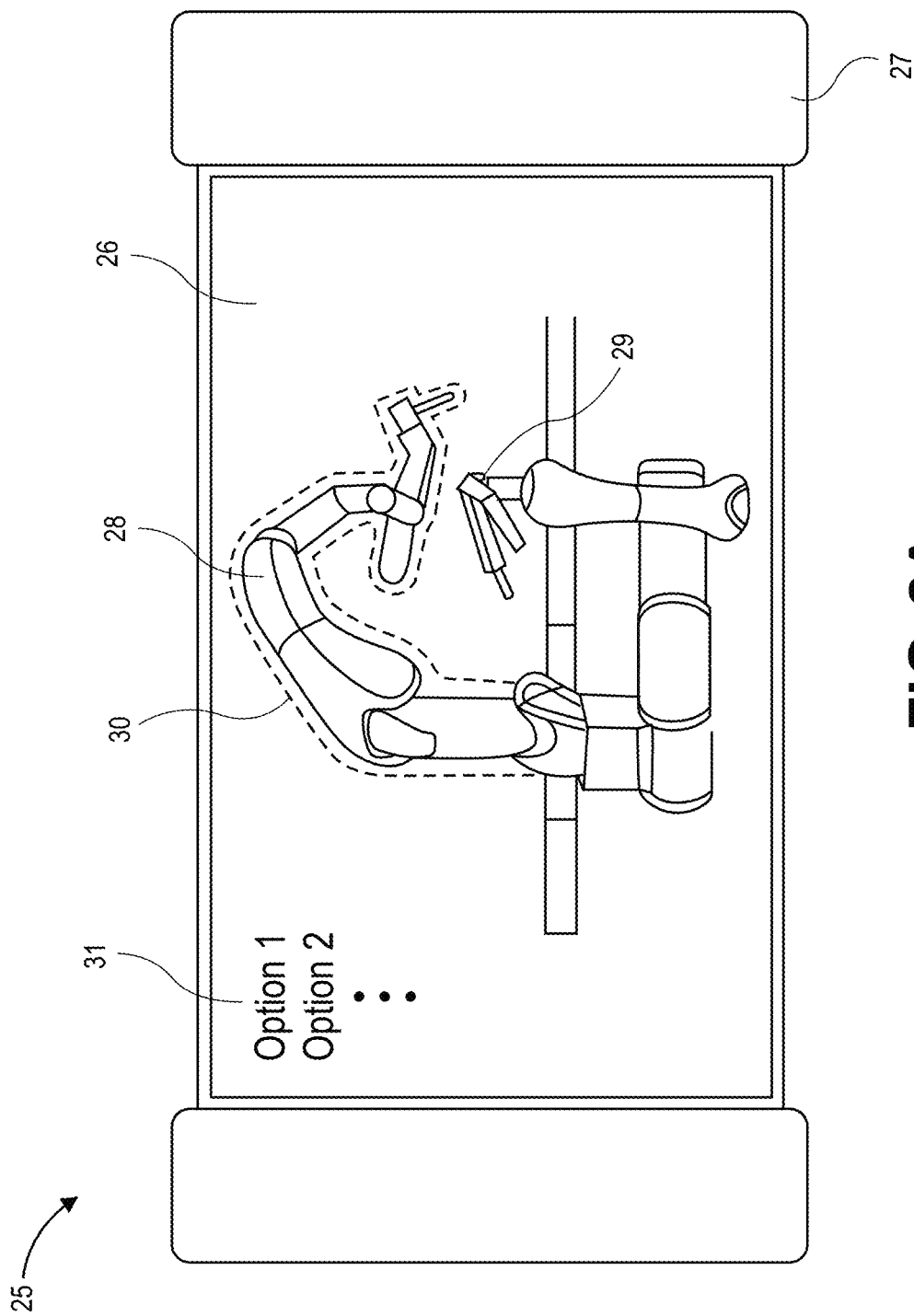
FIG. 2A is a front view of an interface device showing the display in which a robotic arm of the surgical robotic system is visualized to enable identification or selection/targeting of the individual components, in accordance with aspects of the subject technology.

FIG. 2A is a front view 25 of an interface device showing the display in which a robotic arm of the surgical robotic system is visualized to enable identification or selection/targeting of the individual components, in accordance with aspects of the subject technology. The interface device includes a display screen 26 and handles 27. The display screen 26 may display real-time images or videos captured by a camera on the backside of the interface device. The display screen 26 may be a touch screen to allow a user to enter commands, make selections, or manipulate displayed objects. In one aspect, a user may select a target component of the surgical robotic system to control by pointing the interface device at the target component so that the target component appears near the center of the display screen 26. In one aspect, image processing algorithms may process the images or videos captured by the camera to automatically identify a component of the surgical robotic system appearing near the center of the display screen 26 as the target component. In one embodiment, a processor on the interface device may run the image processing algorithms. In another embodiment, a computer of the surgical robotic system such as the control tower 3 of FIG. 1 may run the image processing algorithms. The interface device may transmit the captured images or videos to the surgical robotic system for the remote image processing operations and may receive from the surgical robotic system the identified target component. In one embodiment, a user may identify the target component by touching the target component on the display screen 26.

In one aspect, the image processing algorithms may determine an initial pose or position of the target component. For example, a robotic arm may be folded in a stowed position for storage, extended in a drape position for sterile draping, bent in a preparation position above the patient during pre-operative setup, configured in a pre-docking position ready to be attached to a nearby surgical tool, or in a docked position attached to a surgical tool. The interface device may highlight the target component on the display screen 26 for the user to confirm, for example by highlighting the target component with an engagement indicator. The user may confirm or may reject the target component, in which case the interface device may attempt to identify another component. In one aspect, prior to the user confirming the target component, if the user moves the interface device so the target component is out of the view of the camera, the image processing algorithms may deselect the target component. In another aspect, after the user confirms the target component and while the surgical robotic system is activated to move the target component, if the user moves the interface device so the target component is out of view of the camera, the interface device may deselect the target component and may freeze its movement to prevent the user from moving the target component when it's not the focus of the user's attention.

Based on a confirmed target component and the initial position or pose of the target component, the interface device may generate a list of options for the user to control the position, orientation, movement, function, etc., of the target component. For example, if the user confirms that a robotic arm in the drape position is the target component, the interface device may present a list of options for moving the robotic arm to a predefined preparation or pre-docking position. In one aspect, the list of options may include planned trajectories of the robotic arm to the predefined positions. The interface device may present the list of pre-defined target positions of the target component, the names of the pre-defined target positions (e.g., preparation position, pre-docking position, etc.), or the planned trajectories to the pre-defined target positions as an overlay, for example as an augmented reality (AR) overlay on the display screen 26. The user may select one of the pre-defined target positions as the desired target position of the target component. The interface device may calculate a trajectory for moving the target component from the initial position to the selected target position. In one aspect, the user may select one of the planned trajectories when selecting the desired target position.

In one embodiment, the image processing algorithms may identify another object in the images or videos as a possible destination position for the target component. For example, if a robotic arm in a preparation position is confirmed as the target component, the image processing algorithms may identify a surgical tool in the images or videos as a possible target to which the robotic arm may be attached. The interface device may present the current position or pose of the surgical tool, or a volume in space in the immediate vicinity of the surgical tool as a possible pre-docking destination position for the robotic arm. If the user selects the pre-docking position presented, the interface device may calculate a trajectory for moving the robotic arm from the preparation position to the pre-docking position. The interface device may calculate the trajectory so the robotic arm avoids colliding with or interfering with the operation of other robotic arms. In one aspect, if the planned movement of the robotic arm necessitates moving other robotic arms, the list of options may include one or more planned trajectories for each of multiple robotic arms.

In one embodiment, the user may indicate the destination position directly on the touch screen by, for example, touching the surgical tool displayed. The interface device may highlight the selected surgical tool to request the user to confirm the selection. If confirmed, the interface device may calculate the trajectory for moving the robotic arm to the selected surgical tool and may present the trajectory as an option for the use to select. In one embodiment, a computer of the surgical robotic system such as the control tower may calculate the trajectory instead of the interface device.

Once the user selects an option for moving or changing the position, orientation, or function of the robotic arm, the interface device transmits the selection and information about the trajectory, if any, to the control tower 3 of the surgical robotic system. The user may be prompted to activate the movement of the robotic arm by pressing on a continuous activation button. The interface device may transmit an activation signal to the control tower 3 when the user presses the continuous activation button. Upon receiving the activation signal, the control tower 3 may generate the control signals to activate the actuator 17 to drive the gears, linkages, or joints of the robotic arm to move the robotic arm through the selected trajectory to the destination position. For safety reasons, the user may need to hold the continuous activation button until the robotic arm completes its trajectory to the destination position. If the user releases the continuous activation button, the interface device stops transmitting the activation signal, causing the control tower 3 to stop the motion of the robotic arm. During the move, the display screen 26 may continue to highlight the robotic arm with the engagement indicator to visually indicate to the user that the robotic arm is moving. For added safety, if the user moves the interface device so the robotic arm is out of view of the camera, the interface device may cut off the transmission of the activation signal to stop the movement of the robotic arm to prevent a distracted user from harming the patient.

Referring to FIG. 2A, the display screen 26 shows an example image of a target robotic arm 28 and a second arm 29. The image processing algorithm identifies the target robotic arm 28 appearing in the center of the image as the target component of the surgical robotic system to be controlled. The image processing algorithm determines that the target robotic arm 28 is in a preparation position parked over a patient. The display screen 26 highlights the target robotic arm 28 by enveloping it with an engagement indicator 30. Based on the determination that the target robotic arm 28 is in the preparation position, the display screen 26 displays a list of options 31 for the user to control the position, orientation, movement, function, etc., of the target robotic arm 28. For example, the list of options 31 may include options for moving the target robotic arm 28 to a predefined pre-docking position, to a pre-docking position near a surgical tool, through a planned trajectory, etc. The user may select an option on the display screen 26. Once selected, the engagement indicator 30 may change to a different color, such as green, to indicate that the target robotic arm 28 is ready to be activated. The user may hold a continuous activation button on the back of the interface device to activate the movement of the target robotic arm 28 through its trajectory to the selected destination position. When the target robotic arm 28 completes its trajectory to reach its destination position, the movement stops and the engagement indicator 30 may be turned off to indicate that the target robotic arm 28 is deactivated and deselected.

Figure 2B:
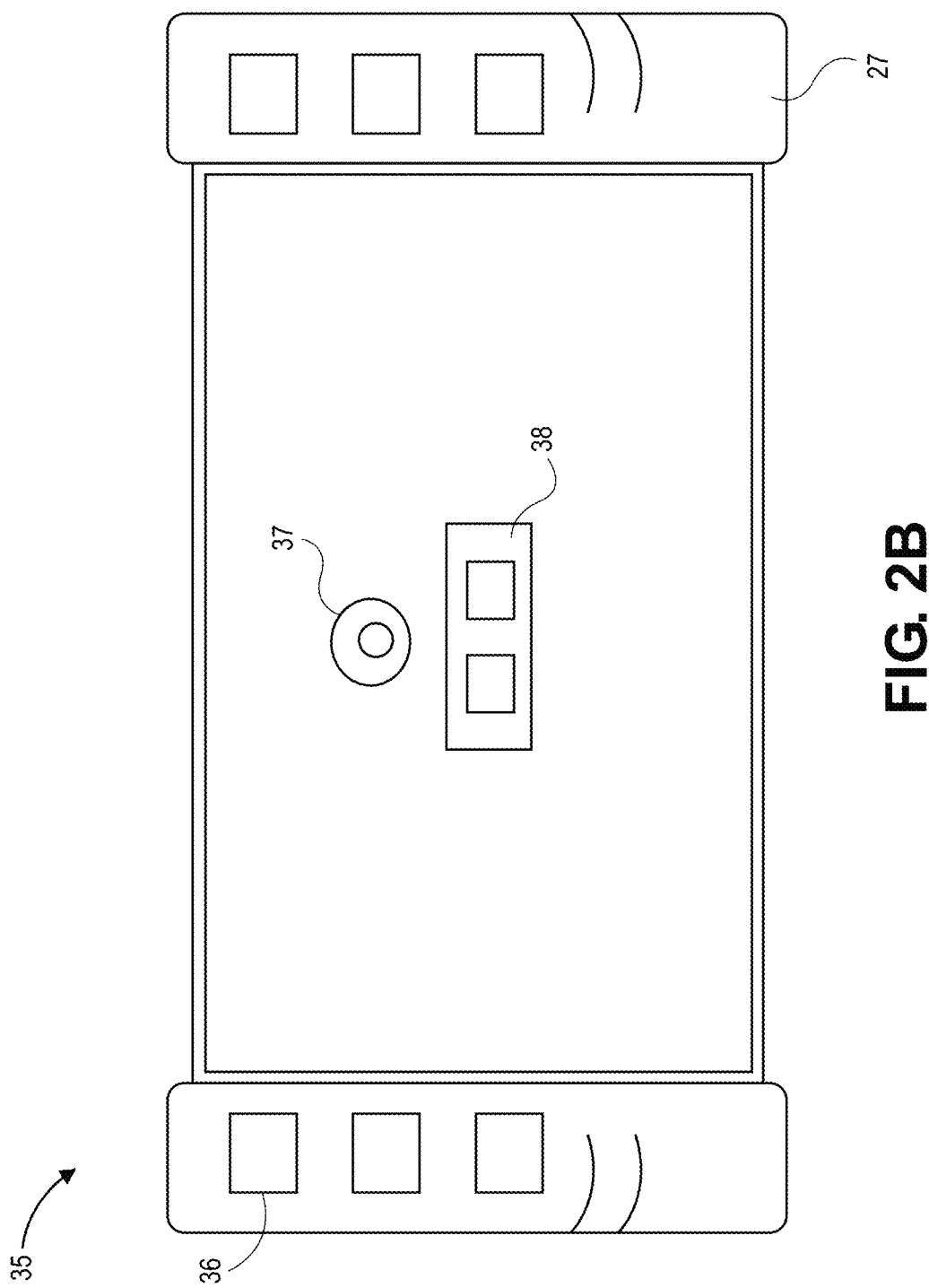
FIG. 2B is a back view of an interface device showing a camera, an optional 3-D camera, and control buttons (which could also be situated on the front or side of the device), in accordance with aspects of the subject technology.

FIG. 2B is a back view 35 of an interface device showing a camera 37, an optional three-dimensional (3-D) camera 38, and control buttons 36, in accordance with aspects of the subject technology. The camera 37 may capture a planar image or video of the surgical robotic system or components thereof to display on the display screen 26 on the front of the interface device. In one embodiment, the interface device may transmit the captured images or videos to the surgical robotic system to display on a remote screen. As discussed, image processing algorithms running on the interface device or the surgical robotic system may process the images or videos to automatically identify a component of the surgical robotic system appearing near the center of the images or videos as a target component to be controlled by a user. Additionally, the image processing algorithms may determine an initial pose or position of the target component. In one embodiment, the image processing algorithms may identify another object in the images or videos as a possible destination position for the target component.

To aid the image processing algorithms in identifying the target component or other objects and their positions, the interface device may have sensors such as the 3-D camera 38 to determine the 3-D positions of components of the surgical robotic system relative to the interface device. For example, the 3-D camera may measure the 3-D positions relative to the interface device of surface points of components of the surgical robotic system. Embodiments of the 3-D camera may include infrared camera tracking system that emits stereo infrared projecting patterns, inertial measurement unit, structured light camera, micro time-of-flight camera, stereo camera, etc. In one embodiment, a surgeon may use the 3-D camera of the interface device to scan a patient on the operating table during pre-operative setup to help the surgeon plan for the surgery using the surgical robotic system.

The control buttons 36 may be placed on both handles 27 to align with control options displayed on the display screen 26. A user may use the control buttons 36 to select a control option to operate a target component. Once a control option is selected, the user may use the control buttons to operate the target component to execute the selected option. In one aspect, the control buttons 36 may be a continuous activation button that needs to be continuously pressed to allow the user to activate the movement of the target component from an initial position through a planned trajectory to a destination position. When the user releases the control buttons, the movement of the target component may stop, even when the target component has not completed its trajectory.

Figure 3:
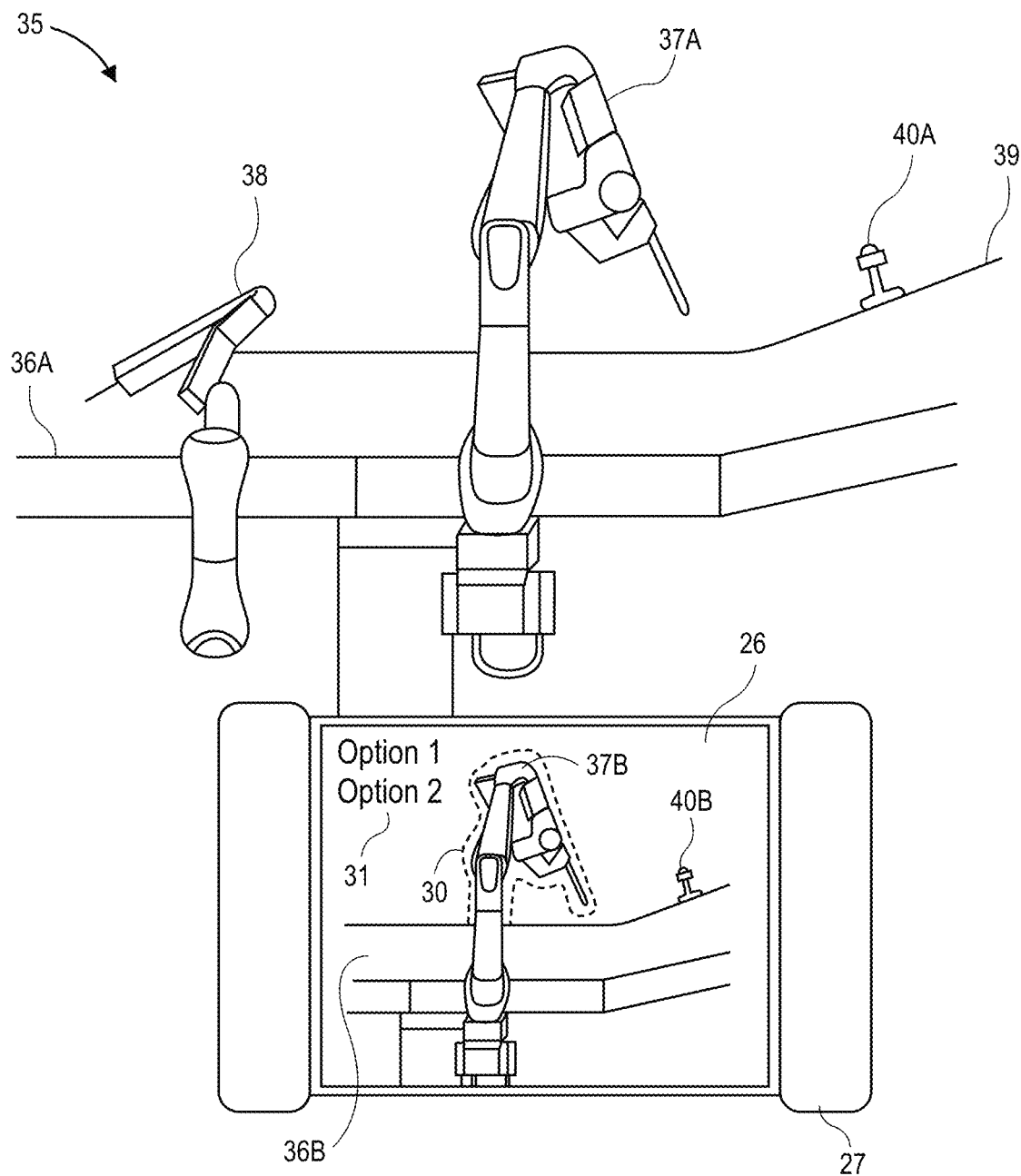
FIG. 3 shows an interface device used to control a robotic arm to move from an initial pose to a final pose, in accordance with aspects of the subject technology.

FIG. 3 shows an interface device used to control a robotic arm to move from an initial pose to a final pose, in accordance with aspects of the subject technology. The operating room environment 35 shows a patient 39 on a table 36A of a surgical robotic system. A first robotic arm 37A and a second robotic arm 38 are positioned on one side of the table 36A. A trocar 40A has been placed on the patient 39 near the first robotic arm 37A.

A user with a direct view of the operating room environment 35 uses the camera of the interface device to capture a real time image or video of the surgical robotic system. The display screen 26 shows an image of the first robotic arm 37B, the table 36B, and the trocar 40B. The second arm 38 is out of view of the camera. The image processing algorithm identifies the first robotic arm 37B appearing in the center of the image as the target component of the surgical robotic system to be controlled. The image processing algorithm determines that the first robotic arm 37B is in a preparation position parked over the patient 39. The display screen 26 highlights the first robotic arm 37B by enveloping it with an engagement indicator 30 of a first color, such as yellow. Based on the determination that the first robotic arm 37B is in the preparation position, the display screen 26 displays a list of options 31 for the user to control the position, orientation, movement, function, etc., of the first robotic arm 37B.

The image processing algorithm may additionally identify the trocar 40B as a possible destination position for the first robotic arm 37B. As such, the list of options 31 may include an option for moving the first robotic arm 37B to a pre-docking position near the trocar 40B, through a planned trajectory. The user may select this option on the display screen 26. Once selected, the engagement indicator 30 may change to a second color, such as green, to indicate that the first robotic arm 37B is ready to be activated. The user may hold a continuous activation button on the back of the interface device to activate the movement of the first robotic arm 37B through its trajectory to the pre-docking position near the trocar 40B. When the first robotic arm 37B completes its trajectory to the pre-docking position, the movement stops and the engagement indicator 30 may be turned off to indicate that the first robotic arm 37B is deactivated and deselected.

The interface device may also be used to select other components of the surgical robotic system. For example, the interface device and the image processing algorithm may identify the table 36B appearing in the center of the image as the target component of the surgical robotic system to be controlled. In one embodiment, the interface device may be used to perform a 3-D scan of a patient on the table during a pre-operative setup to help the surgeon plan for the surgery using the surgical robotic system. The interface device may then be used to control the robotic arms and the table for patient-specific optimal robotic arm and table motion. The interface device may facilitate user selection of the components of the surgical robotic system using virtual representations or augmented reality views. For example, the display screen 26 may display a rendered image or a virtual model of the components, such as a camera view of the components augmented with additional or virtual information.

The interface device may provide other features such as a Web portal (e.g. browser), and may display information such as case setups, surgeon preference cards, instrument lives, documentation, snap shots from endoscope for documentation, photos of patients for documentation, system eIFU, patient data, procedure guide, etc. Other features may include teleconferencing using microphones, speakers, a front facing webcam; service calls using microphones, speakers, a back facing webcam; user authentication using a fingerprint reader and/or an NFC card reader; a docking station to connect to the surgical robotic system such as pairing of a new interface device with the surgical robotic system by sliding in the interface device to the docking station for the surgical robotic system to recognize the interface device; range detection of interface device to control tower using Bluetooth and WiFi to monitor signal strengths of the connections and to trigger alerts when the interface device is too far away.

Figure 4:
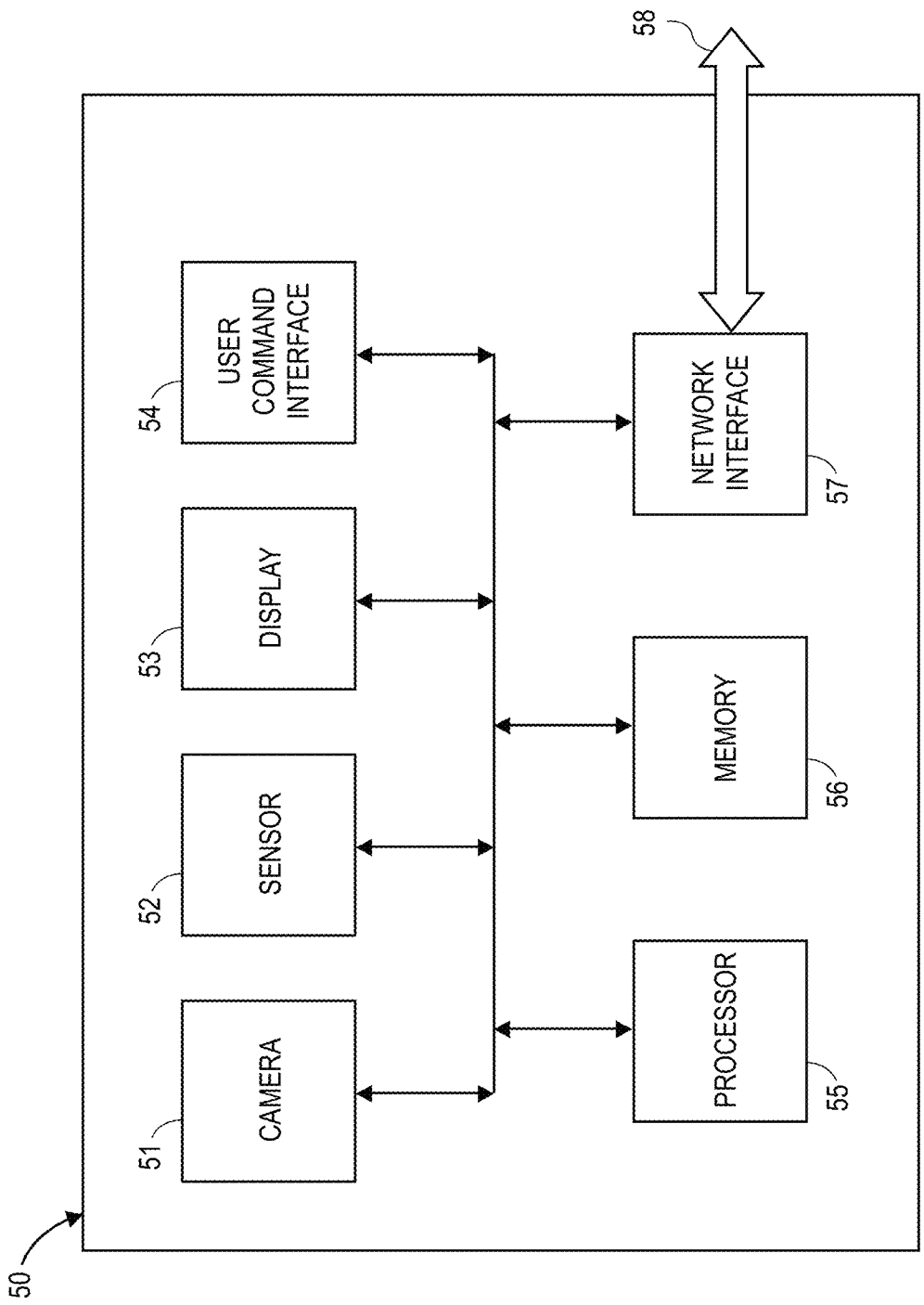
FIG. 4 is a block diagram illustrating exemplary hardware components of an interface device, in accordance with aspects of the subject technology.

FIG. 4 is a block diagram illustrating exemplary hardware components of an interface device 50, in accordance with aspects of the subject technology. The interface device 50 includes a camera 51, sensor 52, display 53, user command interface 54, processor 55, memory 56, and network interface 57. The camera 51 may be configured to capture a planar image or video of the surgical robotic system. The sensor 52 may be a 3-D camera configured to determine the 3-D positions of components of the surgical robotic system relative to the interface device. Images captured by the camera 51 and 3-D positional measurements made by the sensor 52 may be shown on the display 53, which may be a touch screen.

The processor 55 may be configured to run image processing algorithms to process the images captured by the camera 51 and measurements made by the sensor 52 to automatically identify a component of the surgical robotic system appearing near the center of the image as a target component to be controlled by a user. The processor 55 may be configured to run an operating system to control the operation of the interface device 50. The memory 56 may store the image processing algorithms, operating system, program codes, and other data memories used by the processor 55. The user command interface 54 may include the continuous activation button used by the user to select a control option to operate a target component and to execute the selected option to move the target component to its destination position.

The hardware components may communicate via a bus. The interface device may use the network interface 57 to communicate with the surgical robotic system through an external interface 58. The external interface 58 may be a wireless or a wired interface.

Figure 5:
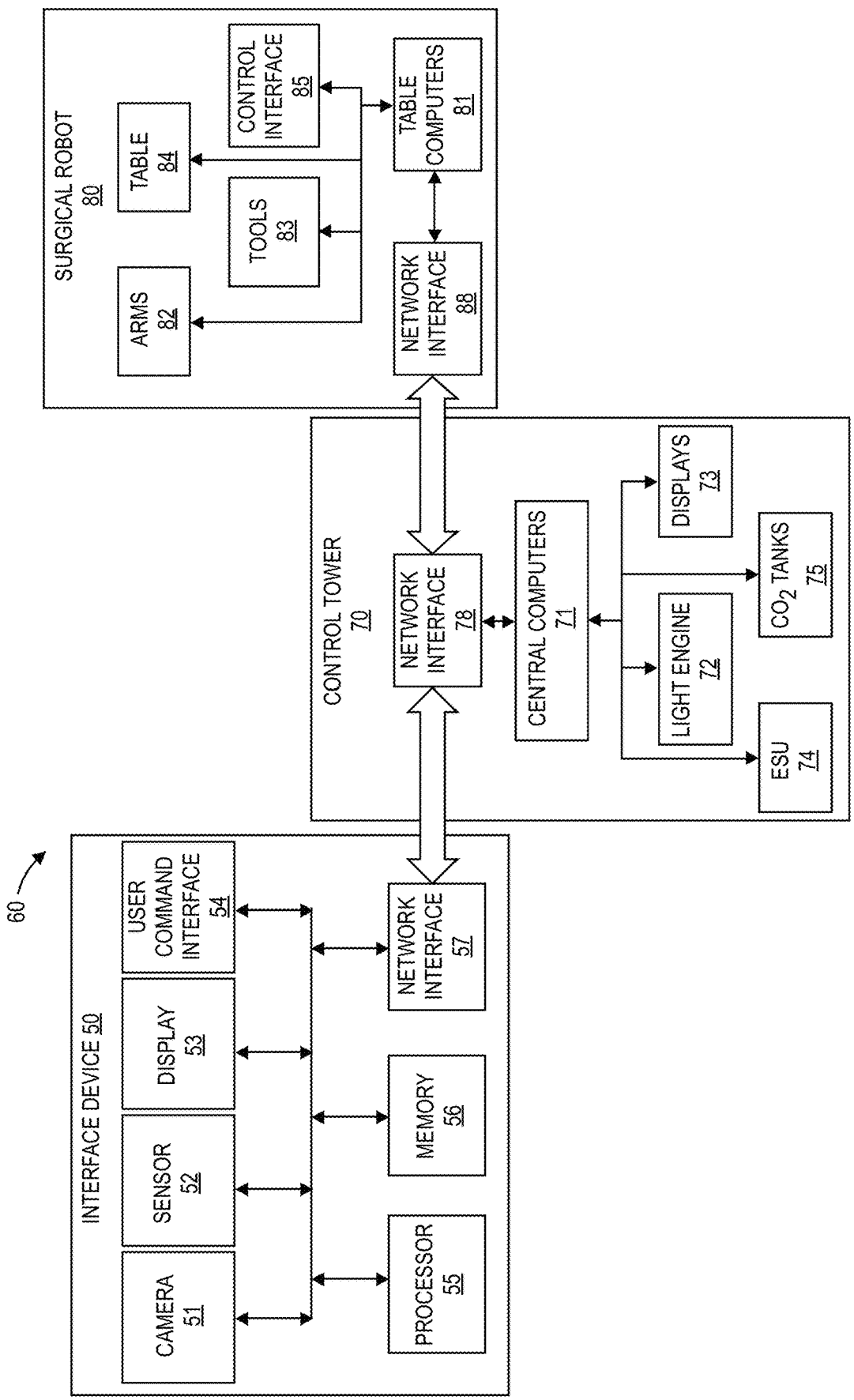
FIG. 5 is a block diagram illustrating exemplary hardware components of a surgical robotic system, in accordance with aspects of the subject technology.

FIG. 5 is a block diagram illustrating exemplary hardware components of a surgical robotic system 60, in accordance with aspects of the subject technology. The exemplary surgical robotic system 60 may include an interface device 50, a surgical robot 80, and a control tower 70. The interface device 50 has been discussed in regard to FIG. 4 and is not repeated. The surgical robotic system 60 may include other or additional hardware components; thus, the diagram is provided by way of example and not a limitation to the system architecture.

The control tower 70 may be a mobile point-of-care cart housing touchscreen displays, computers that control the surgeon's robotically-assisted manipulation of instruments, safety systems, graphical user interface (GUI), light source, and video and graphics computers. As shown in FIG. 5, the control tower 70 may comprise central computers 71 that may include at least a visualization computer, a control computer, and an auxiliary computer, various displays 73 that may include a team display and a nurse display, and a network interface 78 coupling the control tower 70 to both the interface device 50 and the surgical robot 80. The control tower 70 may also house third-party devices, such as an advanced light engine 72, an electrosurgical generator unit (ESU) 74, and insufflator and CO2 tanks 75. The control tower 70 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 80 comprises an articulated operating table 84 with a plurality of integrated arms 82 that may be positioned over the target patient anatomy. A suite of compatible tools 83 may be attached to or detached from the distal ends of the arms 82, enabling the surgeon to perform various surgical procedures. The surgical robot 80 may also comprise control interface 85 for manual control of the arms 82, operating table 84, and tools 83. The control interface 85 may include items such as, but not limited to, remote controls, buttons, panels, and touchscreens. Other accessories such as trocars (sleeves, seal cartridge, and obturators) and drapes may also be manipulated to perform procedures with the system. In one embodiment, the plurality of the arms 82 may include four arms mounted on both sides of the operating table 84, with two arms on each side. For certain surgical procedures, an arm mounted on one side of the operating table 84 may be positioned on the other side of the operating table 84 by stretching out and crossing over under the operating table 84 and arms mounted on the other side, resulting in a total of three arms positioned on the same side of the operating table 84. The surgical tool may also comprise table computers 81 and a network interface 88, which may place the surgical robot 80 in communication with the control tower 70.

Figure 6:
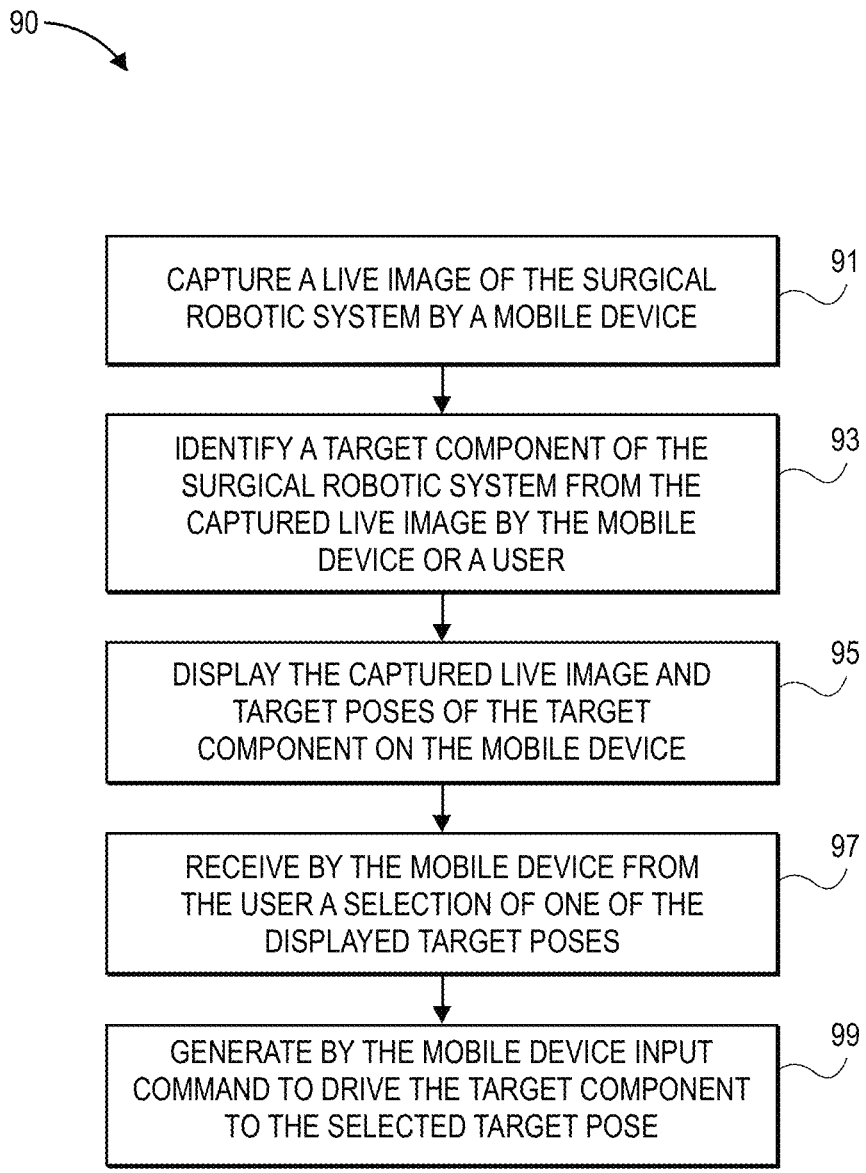
FIG. 6 is a flow chart illustrating a method of controlling a surgical robotic system using a mobile device, in accordance with aspects of the subject technology.

FIG. 6 is a flow chart illustrating a method 90 of controlling a surgical robotic system using a mobile device, in accordance with aspects of the subject technology. The mobile device may be the interface device of FIG. 2A, FIG. 2B, or FIG. 4.

In block 91, the mobile device may capture a live image of a portion of the surgical robotic system. The mobile device may use a camera to capture a planar image or video of components of the surgical robotic system to display on the screen.

In block 93, the mobile device or a user may identify a target component of the surgical robotic system from the captured live image. For example, a user may select a target component of the surgical robotic system to control by pointing the mobile device at the target component so that the target component appears near the center of the display screen. An image processing algorithm running on the mobile device or on the control tower may process the captured live image to identify the target component.

In block 95, the mobile device may display the captured live image, the target component, and possible target poses of the target component on the screen. For example, the mobile device may highlight a robotic arm as the target component on the screen by displaying a visual indicator that outlines the robotic arm or by rendering an image of the robotic arm overlaid with augmented or virtual information. In another aspect, the mobile device may run an image processing algorithm on the captured live image to identify one or more objects with which the robotic arm may engage as possible target poses for the robotic arm.

In block 97, the mobile device may receive from the user an input to select one of the displayed target poses for the target component. For example, the user may indicate on the touchscreen a pre-docking destination position for the robotic arm. In other aspects, the user may use the touchscreen to select an option for moving or changing the position, orientation, or function of the robotic arm.

In block 98, the mobile device may generate an input command to drive the target component to the selected target pose. For example, the mobile device may transmit an activation signal to the control tower for the control tower to generate the control signals to activate the actuator to drive the gears, linkages, or joints of the robotic arm through a calculated trajectory to the selected destination position. In one aspect, the mobile device or the control tower may calculate the trajectory for moving the robotic arm from an initial pose to the destination pose. The trajectory may be calculated so the robotic arm avoids colliding with or interfering with the operations of other robotic arms.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

The invention claimed is:

1. A mobile interface device for a surgical robotic system, comprising:
   a camera configured to capture a live image of a portion of the surgical robotic system;
   a processor configured to:
     process the captured live image to identify a target component of the surgical robotic system to be controlled using the mobile interface device; and
     determine a current pose of the target component;
   a display configured to:
     display the captured live image; and
     display one or more target poses of the target component; and
   one or more control interfaces configured to:
     allow a user to select one of the target poses; and
     generate an input command to drive the target component from the current pose to the selected target pose.

2. The mobile interface of claim 1, wherein the display is further configured to present information to visually indicate the one or more target poses of the target component to the user.

3. The mobile interface device of claim 1, wherein the processor is further configured to determine a plurality of command options for controlling the target component and the display is further configured to display the plurality of command options for the user to control the target component.

4. The mobile interface device of claim 1, wherein the processor is further configured to process the captured live image to identify a second component of the surgical robotic system, and the display is further configured to display information to indicate a current pose of the second component as one of the target poses of the target component.

5. The mobile interface device of claim 1, wherein the processor is further configured to determine a trajectory to drive the target component from the current pose to the selected target pose.

6. The mobile interface device of claim 1, further comprising one or more sensors configured to measure a three-dimensional position relative to the interface device of a plurality of surface points of the surgical robotic system captured in the live image, and wherein the processor is further configured to process the plurality of measured three-dimensional positions of the surface points of the surgical robotic system captured in the live image to identify the target component.

7. The mobile interface device of claim 1, wherein the camera comprises a 3-dimensional camera configured to scan a patient on an operating table of the surgical robotic system during a pre-operative setup, wherein the processor is further configured to process scanned information of the patient to determine a patient-specific movement of the target component.

8. The mobile interface device of claim 1, wherein the one or more control interfaces is further configured to generate a second input command to freeze a movement of the target component when the target component moves off the captured live image.

9. The mobile interface device of claim 1, wherein the display is further configured to display a visual indication of the target component to allow the user to confirm the target component.

10. The mobile interface device of claim 1, wherein the display is a touch-screen display and wherein the touch-screen display is configured to allow the user to select a current pose of a second component of the surgical robotic system in the captured live image as a desired target pose of the target component.

11. A method for controlling a surgical robotic system, comprising:
    capturing, using a mobile device, a live image of a portion of the surgical robotic system;
    identifying, by the mobile device or by a user, a target component of the surgical robotic system from the captured live image;
    displaying, by the mobile device, the captured live image and one or more target poses of the target component;
    receiving, by the mobile device from the user, a selected target pose from the one or more target poses displayed; and
    generating, by the mobile device, an input command to drive the target component from a current pose to the selected target pose.

12. The method of claim 11, wherein the displaying, by the mobile device, the one or more target poses of the target component comprises presenting information about the one or more target poses.

13. The method of claim 11, further comprising:
generating, by the mobile device, a plurality of command options for controlling the target component; and
displaying, by the mobile device, the plurality of command options for the user to control the target component.

14. The method of claim 11, further comprising:
identifying, by the mobile device, a second component of the surgical robotic system from the captured live image; and
displaying, by the mobile device, information to indicate a current pose of the second component as one of the target poses of the target component.

15. The method of claim 11, further comprising:
determining, by the mobile device, a trajectory to drive the target component from the current pose to the selected target pose.

16. The method of claim 11, further comprising:
scanning a patient on an operating table of the surgical robotic system during a pre-operative setup to obtain three-dimensional information of the patient; and
processing the three-dimensional information of the patient to determine a patient-specific movement of the target component.

17. The method of claim 11, further comprising:
generating, by the mobile device, a second input command to freeze a movement of the target component when the target component moves off the captured live image.

18. The method of claim 11, further comprising:
displaying, by the mobile device, a visual indication of the target component to allow the user to confirm the target component.

19. A surgical robotic system, comprising:
an operating table;
a plurality of robotic arms coupled to the operating table;
a mobile interface device configured to:
  capture a live image of the operating table or the plurality of robotic arms;
  display a rendered image of the operating table or the plurality of robotic arms from the live image;
  receive user input to control the operating table or one of the robotic arms; and
  generate an input command to control the operating table or one of the robotic arms in response to the user input; and
a control tower communicatively coupled to the mobile interface device, the operating table and the plurality of robotic arms, wherein the control tower is configured to:
  receive the input command from the mobile interface device; and
  generate a control command to manipulate the operating table or one of the robotic arms in response to the input command.

20. The surgical robotic system of claim 19, wherein the mobile interface device is further configured to present a plurality of input command options to control the operating table or one of the robotic arms.

* * * * *